United States Patent
Hestdal

(10) Patent No.: US 11,066,478 B2
(45) Date of Patent: *Jul. 20, 2021

(54) INTRAVESICAL THERAPY FOR BLADDER CANCER

(71) Applicant: PHOTOCURE ASA, Oslo (NO)

(72) Inventor: Kjetil Hestdal, Oslo (NO)

(73) Assignee: PHOTOCURE ASA, Oslo (NO)

( * ) Notice: Subject to any disclaimer, the term of this patent is extended or adjusted under 35 U.S.C. 154(b) by 0 days.

This patent is subject to a terminal disclaimer.

(21) Appl. No.: 16/388,379

(22) Filed: Apr. 18, 2019

(65) Prior Publication Data

US 2019/0241672 A1 Aug. 8, 2019

Related U.S. Application Data

(63) Continuation of application No. 16/063,169, filed as application No. PCT/EP2016/081798 on Dec. 19, 2016, now abandoned.

(30) Foreign Application Priority Data

Dec. 17, 2015 (GB) ...................... 1522311

(51) Int. Cl.

| C07K 16/28 | (2006.01) |
| A61K 39/395 | (2006.01) |
| A61K 41/00 | (2020.01) |
| A61P 35/00 | (2006.01) |
| C07K 16/30 | (2006.01) |
| A61K 39/00 | (2006.01) |

(52) U.S. Cl.

CPC .......... *C07K 16/30* (2013.01); *A61K 41/0061* (2013.01); *A61P 35/00* (2018.01); *C07K 16/2818* (2013.01); *C07K 16/2827* (2013.01); *A61K 2039/54* (2013.01)

(58) Field of Classification Search

None

See application file for complete search history.

(56) References Cited

U.S. PATENT DOCUMENTS

| 10,556,010 B2 | 2/2020 | Hestdal | |
| 2006/0110383 A1 | 5/2006 | Honjo et al. | |
| 2018/0318365 A1 | 11/2018 | Yeung et al. | |
| 2018/0371101 A1* | 12/2018 | Hestdal | A61K 41/0061 |
| 2019/0241672 A1 | 8/2019 | Hestdal | |
| 2020/0155683 A1 | 5/2020 | Hestdal | |

FOREIGN PATENT DOCUMENTS

| WO | 96/28412 A1 | 9/1996 |
| WO | 2004/004771 A1 | 1/2004 |
| WO | 2005/092838 A1 | 10/2005 |
| WO | 2008/156712 A1 | 12/2008 |
| WO | 2009/114335 A2 | 9/2009 |
| WO | 2010/077634 A1 | 7/2010 |
| WO | 2013/019906 A1 | 2/2013 |
| WO | 2013/079174 A1 | 6/2013 |
| WO | 2013/181452 A1 | 12/2013 |

OTHER PUBLICATIONS

Choi, W. et al., "Identification of District Basal and Lumina Subtypes of Muscle-Invasive Bladder Cancer with Different Sensititives to Frontline Chemotherapy"; Cancer Cell (2014); vol. 25; pp. 152-165.

Clinical trial NCT02808143 (accessed at https://clinicaltrials.govict2/show/NCT02808143?term=NCT02808143&draw=2&rank=1 on Jul. 9, 2020), 14 pages.

Clinical trial NCT03759496 (accessed at https://clinicaltrials.govict2/show/NCT03759496?term=NCT03759496&draw=2&rank=1 on Jul. 9, 2020), 9 pages.

Clinical trial NCT03167151 (accessed at https://clinicaltrials.govict2/show/NCT03167151?term=NCT03167151&draw=2&rank=1 on Jul. 16, 2020), 11 pages.

Woodcook, V. K., et al., A Phase I Study to Assess the Safety and Tolerability of Intravesical Pembrolizumba in Recurrent Non-Muscle Invasive Bladder Cancer (NMIBC); Journal of Clinical Oncology (2019); vol. 37:7(suppl) Abs. 406 (3 pgs.).

Jokisch, F. et al., "Intravesical Immunotheraphy in Nonmuscle Invasive Bladder Cancer"; Indian Journal of Urology (2015); vol. 31:4; pp. 304-311.

Hanna, K. S., et al., "Updates and Novel Treatments in Urothelial Carcinoma"; Journal of Oncology Pharmacy Practice (2018); vol. 25:3; pp. 648.656.

Philips, G. K et al., "Therapeutic Uses of Anti-PD-1 and Anti-PD-L-1 Antibodies"; International Immunology (2014); vol. 27:1; pp. 39-46.

Powles, T. et al., "MPDL3280A (anti-PD-L1) Treatment Leads to Clinical Activity in Metastatic Bladder Cancer"; Nature (2014); vol. 515; 12 pgs.

Rink, M. et al., "Hexyl Aminolevulinate-Guided Fluorescence Cystoscopy in the Diagonisis and Follow-up of Patients with Non-Muscle-Invasive Bladder Cancer; A Critical Review of the Current Literature"; European Urology (2013); vol. 34; pp. 624-638.

(Continued)

*Primary Examiner* — Ilia I Ouspenski

(74) *Attorney, Agent, or Firm* — Fox Rothschild LLP

(57) ABSTRACT

This invention relates to an intravesical therapy for bladder cancer.

20 Claims, No Drawings

(56) References Cited

OTHER PUBLICATIONS

Witjes, J.A. et al., "Clinical Cost Effectivenes of Hexaminolevulinate-guided Blue-light Cystoscopy: Eviddence Review and Updated Expert Recommmendations"; European Urology (2014)I vol. 66; pp. 863-871.
Gakis, G. et al., "Photodynamic Diagnosis-guided TUR-BT is an Independent Predictor for Improved Recurrence-free Survival and Radical Cystectomy for Invasive Bladder Cancer"; Urology (2013); vol. 82 (3 Supplemental 1); pp. S208; Abstract No. UP:046.
Sundararajan, S. et all., "Anti-PD-1 and PD-L1 Therapy for Bladder Cancer: What is on the Horizon?" Future Oncology (2015); vol. 11:16; pp. 2299-2306.
Saylor, B. P., "Product Review: Agreement Reached for Phase III Clinical Trial of Bladder Ca Agent"; Urorlogy Times (2017); Internet Publication 2 pgs.
Jokisch, J.F., et al., "Intavesical Immunotherapy in Nonmuscle Invasive Bladder Cancer"; Indian J. Urology (2015); vol. 31:4; pp. 304-311.
Hurwitz, M E. et al., "The Effective of BCG Intravesical Therapy and Recurrence on PDL1 Expression in Non-Invasive Bladder Cancers"; J. Clin. Oncol (2015); vol. 33 (Suppl; abstract e15504); 3 pgs.
Bader. M. J. et al., "Photodynamic Therapy of Bladder Cancer—A Phase I Study Using Hexaminolevulinate (HAL)", Urologic Oncology: Seminars and Origional Investigations (2013); vol. 31; pp. 1178-1183.
(Author: unknown): "Role of Anti-PD-1/PD-L1 Immunotherapy in Bladder Cancer"; Onclive Insights (2015); Special Issues, vol. 1:1; 12 pgs; https://www.onclive.com/view/role-of-anti-pd-1-pd-l1-immunotherapy-in-bladder-cancer.

\* cited by examiner

INTRAVESICAL THERAPY FOR BLADDER CANCER

This invention relates to an intravesical (i.e. inside the bladder) therapy for bladder cancer.

Bladder cancer is the ninth most common cancer diagnosis worldwide, with more than 330 000 new cases each year and more than 130 000 deaths per year. At any point in time, 2.7 million people have a history of urinary bladder cancer.

The diagnosis of bladder cancer ultimately depends on cystoscopic examination of the bladder (cystoscopy) and histological evaluation of the resected tissue. In general, cystoscopy is initially performed in the office, using flexible instruments. At the initial diagnosis of bladder cancer, 70% of cases are diagnosed as non-muscle-invasive bladder cancer (NMIBC) and approximately 30% as muscle-invasive bladder cancer (MIBC).

If a bladder tumor has been detected during cystoscopy, the patient will undergo transurethral resection (TUR), i.e. a procedure where the bladder is visualized through the urethra and tumors and lesions are resected. In case of NMIBC, such a resection is to completely remove the tumor, in case of MIBC; such a resection is of a palliative nature. Apart from the resection of the tumor, the TUR is also carried out to enable a correct histological diagnosis of the resected tumor/tumor biopsies by a pathologist.

For patients with MIBC, the standard treatment for is radical cystectomy, i.e. removal of the bladder and adjacent organs, that is prostate and seminal vesicles in men, and uterus and adnexa in women. It also includes the dissection of regional lymph nodes. Cystectomy is also advocated in patients with NMIBC who are at high risk of progression, i.e. patients having multiple recurrent high-grade tumors or high-grade T1 tumors or high-grade tumors with concurrent carcinoma-in-situ (CIS). Further, cystectomy is advocated in patients with NMIBC who have received Bacillus Calmette-Guérin (BCG) immunotherapy but where such treatment has failed.

Although being the gold standard for MIBC treatment and advocated in patients with certain types of NMIBC, radical cystectomy only provides 5-year survival in about 50% of patients. In order to improve these unsatisfactory results, the use of neoadjuvant therapies has been explored since the 1980s.

Currently, neoadjuvant radiotherapy and neoadjuvant chemotherapy is used. With neoadjuvant radiotherapy, down staging of the cancer after radiotherapy takes about 4-6 weeks. However, a delay of surgery in patients with locally advanced bladder cancer beyond 90 days has shown to cause a significant increase in extravesical disease (81 vs 52%). Neoadjuvant radiotherapy is not recommended according to the current European guidelines on MIBC since no data exist to support that neoadjuvant radiotherapy for operable MIBC increases survival.

Neoadjuvant chemotherapy has many advantages including that chemotherapy is delivered at the earliest time-point, when the burden of micrometastatic disease is expected to be low; that tolerability of chemotherapy is expected to be better before cystectomy rather than after; and that hypothetically patients with micrometastatic disease might respond to neoadjuvant therapy and reveal favorable pathological status determined mainly by negative lymph node status and negative surgical margins. Neoadjuvant cisplatin-containing chemotherapy has shown to significantly improve survival (5% absolute improvement in survival at 5 years). However, as stated above, delayed cystectomy may compromise the outcome in patients who are not sensitive to chemotherapy and generally, pre-operative anemia and neuropathy is more common in patients receiving neoadjuvant chemotherapy prior to cystectomy. The current European guidelines on MIBC state that ". . . neoadjuvant chemotherapy has its limitations regarding patient selection, current development of surgical technique, and current chemotherapy combinations." Hence, there is room for improvement of neoadjuvant therapies for bladder cancer patients who are scheduled for a cystectomy, i.e. bladder cancer patients diagnosed with MIBC or NMIBC who are at high risk of progression, including multiple recurrent high-grade tumors or high-grade T1 tumors or high-grade tumors with concurrent carcinoma-in-situ (CIS).

For patients with NMIBC, the standard treatment is resection of the tumor by TUR. Instillation into the bladder of a patient of a composition comprising HAL or a pharmaceutically acceptable salt thereof and exposing the inside of said bladder to blue light may be used to improve visualization of bladder cancer during cystoscopy and/or TUR. As a standard procedure, cystoscopy and TUR are performed using white light. However, since the use of white light can lead to missing lesions that are present but not visible, photodynamic diagnosis (PDD) is often used in such procedures. PDD involves the administration of a photosensitizer or a precursor thereof (i.e. a "photosensitizing agent") to an area of interest. The photosensitizer or precursor thereof is taken up into the cells, where a precursor of a photosensitizer is converted into an active photosensitizer. Upon exposure of the area of interest to light of a suitable wavelength, the photosensitizer is excited and, upon relaxation to its ground state, fluorescence occurs.

Hexyl 5-ALA ester (hexaminolevulinate, HAL) and its salts are such photosensitizing agents. HAL preferably penetrates rapidly proliferating cells, e.g. tumor cells, where it is converted into porphyrins, which are photosensitizers and fluorescent compounds. Under subsequent blue-light illumination, the porphyrins emit red light and thus enable specific and accurate visualization of the tumor. Hexvix® (Photocure ASA, Norway), in the US and Canada marketed as Cysview® is a commercially available approved drug that comprises HAL and is used in PDD in cystoscopy and TUR procedures.

In patients with NMIBC, HAL-guided cystoscopy and TUR has increased detection of both papillary tumors and flat carcinoma-in-situ (CIS) lesions, the latter of which are difficult to detect with white light alone. HAL-guided TUR of bladder cancer in patients with NMIBC has further reduced the rate of residual tumor after such procedures and has led to superior recurrence free survival (RFS) rates and prolonged RFS intervals compared to white light TUR alone (see Rink M, et al. Eur Urol 4(64), 2013, 624). Existing European guidelines on NMIBC and several expert groups consensus statements recommend the use of HAL-guided TUR in various settings of management of NMIBC and some even recommend its use in all NMIBC patients at initial TUR (see Witj es JA, et al., Eur Urol 1(66), 2014, 863).

Although a TaT1 tumor can be completely resected by HAL-guided TUR, and HAL-guided TUR favorably affects recurrence rate, these tumors may recur and progress to muscle-invasive bladder cancer in a limited number of cases. It is therefore necessary to consider adjuvant therapy, i.e. adjuvant chemotherapy or adjuvant chemotherapy and adjuvant immunotherapy, in all patients. The choice of therapy may be considered differently according to what risk is acceptable for the individual patient. Usually, a patient will receive one immediate, post-TUR instillation of chemotherapy into the bladder. The need for further adjuvant intravesical therapy depends on the patients' prognosis. In patients with a low risk of tumor recurrence, a single immediate instillation reduces the risk of recurrence and is considered as the standard treatment, i.e. no further treatment is given in these patients before recurrence. For other patients, however, a single immediate instillation remains an incomplete treatment because the likelihood of recurrence and/or progression is considerable. There is no single chemotherapy drug that is superior with regard to efficacy; mitomycin C, epirubicin, and doxorubicin have all shown a beneficial effect. However, mitomycin C (MMC) is often the drug of choice.

According to EAU guidelines for the treatment of NMIBC, in patients with TaT1 tumors at intermediate or high risk of recurrence and intermediate or high risk of progression, one immediate instillation of chemotherapy should be followed by a minimum one year of Bacillus Calmette-Guérin (BCG) immunotherapy, or by further instillations of chemotherapy. In patients with bladder CIS, intravesical BCG for at least one year is indicated.

Assuming that maintenance therapy with BGC is necessary for optimal efficacy, the issue of BCG toxicity becomes more relevant. As a result of the more pronounced side effects of BCG compared to intravescial chemotherapy, there is still a reluctance about the use of BCG. Deaths due to BCG sepsis and the high frequency of BCG-induced cystitis and allergic reactions have compromised its use. In addition, treatment failure of BCG is not uncommon.

In view of the above, there is a high need of new types of adjuvant and neoadjuvant therapy for the management of bladder cancer.

Such a new therapy includes the use of anti-PD-L1 antibodies. Anti-PD-L1 is an investigational monoclonal antibody designed to interfere with a protein called PD-L1. Anti-PD-L1 targets PD-L1 expressed on cancer cells and tumor-infiltrating immune cells, preventing it from binding to PD-1 and B7.1 on the surface of T cells. By inhibiting PD-L1, anti-PD-L1 may enable the activation of T cells, restoring their ability to effectively detect and attack cancer cells, e.g. bladder cancer cells.

Another new therapy includes the use of anti-PD-1 antibodies, preferably anti-PD-1 antibodies. Anti-PD-1 is an investigational monoclonal antibody that binds to the PD-L1 (programmed death-ligand 1) protein, which is present at high levels in many cancer types, e.g. bladder cancer. By competitively blocking the interaction with PD-1 receptors, it is believed that anti-PD-1 thereby restores anti-cancer T-cell responses.

Thus, anti-PD-L1 antibodies and anti-PD-1 antibodies target different components of the same interaction mechanism between immune cells (specifically killer T cells) and cancer cells, but have a similar therapeutic effect: anti-PD-L1 antibodies target PD-L1 (programmed death ligand-1) expressed on cancer cells while anti-PD-1 antibodies target the other half of this mechanism, PD-1 (programmed death receptor-1), which is expressed on killer T cells.

Both anti-PD-L1 antibodies and anti-PD-1 antibodies are for mainly for parenteral or intravenous administration. Such administrations may lead to side effects due to systemic distribution of the drug.

We now suggest that anti-PD-L1 antibodies and/or anti-PD-1 antibodies are used for intravescial therapy in patients with bladder cancer.

Hence, in a first aspect the invention provides a method of therapy for bladder cancer in a bladder cancer patient comprising the installation into the bladder of said patient of a composition comprising anti-PD-L1 antibodies and/or anti-PD-1 antibodies.

In an alternative first aspect, the invention provides a composition comprising anti-PD-L1 antibodies and/or anti-PD-1 antibodies for use in a method of therapy for bladder cancer, wherein said composition is instilled into the bladder of a patient with bladder cancer.

The term "anti-PD-L1 antibodies and/or anti-PD-1 antibodies" means that the composition for use in the invention either comprises anti-PD-L1 antibodies or comprises anti-PD-1 antibodies or comprises both anti-PD-L1 antibodies and anti-PD-1 antibodies.

Preferred anti-PD-L1 antibodies are those by Roche, preferably MPDL3280A. Said preferred anti-PD-L1 antibodies are described in WO 2010/077634, WO 2013/019906 and WO 2013/181452, the entire contents of which are incorporated herein by reference.

Preferred anti-PD-1 antibodies are those by Merck, preferably pembrolizumab (Keytruda). Such preferred anti-PD-1 antibodies are described in WO2008/156712, WO 2009/114335 and WO 2013/079174, the entire contents of which are incorporated herein by reference.

Other preferred anti-PD-1 antibodies are those by Bristol-Myers Squibb, preferably nivolumab (Opdivo). Such preferred anti-PD-1 antibodies are described in WO 2004/004771, the entire contents of which are incorporated herein by reference.

The bladder cancer in the context of the invention is either muscular invasive bladder cancer (MIBC) or non-muscular invasive bladder cancer (NMIBC).

For patients who are scheduled for a cystectomy, i.e. who either have MIBC or NMIBC with a high risk of progression, including multiple recurrent high-grade tumors or high-grade T1 tumors or high-grade tumors with concurrent carcinoma-in-situ (CIS), the therapy according to the invention is a neoadjuvant therapy. The term "neoadjuvant therapy" means the administration of a therapeutic agent before/prior to the main treatment for the disease. In the context of the invention, the main treatment for such patients is cystectomy and the disease is MIBC or NMIBC with a high risk of progression, including multiple recurrent high-grade tumors or high-grade T1 tumors or high-grade tumors with concurrent carcinoma-in-situ (CIS).

Hence, in one embodiment, the invention provides a method of neoadjuvant therapy for bladder cancer in a bladder cancer patient who is scheduled for a cystectomy, comprising the installation into the bladder of said patient of a composition comprising anti-PD-L1 antibodies and/or anti-PD-1 antibodies.

In an alternative embodiment, the invention provides a composition comprising anti-PD-L1 antibodies and/or anti-PD-1 antibodies for use in a method of neoadjuvant therapy for bladder cancer, wherein said composition is instilled into the bladder of a bladder cancer patient who is scheduled for a cystectomy.

For patients with NMIBC where cystectomy is not advocated, e.g. who have TaT1 tumors with low risk of recurrence and progression, or TaT1 tumors with intermediate or high risk of recurrence and intermediate risk of progression or CIS, the therapy according to the invention is an adjuvant therapy. The term "adjuvant therapy" means the administration of a therapeutic agent in addition to the main treatment for the disease. In the context of the invention, the main treatment for such patients is TUR and the disease is NMIBC where cystectomy is not advocated.

Hence, in a further embodiment, invention provides a method of adjuvant therapy for bladder cancer in a bladder cancer patient who undergoes TUR, comprising the instillation into the bladder of said patient of a composition comprising anti-PD-L1 antibodies and/or anti-PD-1 antibodies.

In an alternative further embodiment, the invention provides a composition comprising anti-PD-L1 antibodies and/or anti-PD-1 antibodies for use in a method of adjuvant therapy for bladder cancer, wherein said composition is instilled into the bladder of a bladder cancer patient who undergoes TUR.

The adjuvant therapy according to the invention can be carried out prior, simultaneously or after said TUR.

The composition for use in the invention may comprise pharmaceutically acceptable carriers, excipients, or stabilizers. The composition for use in the invention is preferably a semi-solid composition or a liquid composition. The term "semi-solid" denotes a physical state which is neither solid nor liquid. Semi-solids (or quasi-solids) are similar to a solid in some respects, e.g. a semi-solid can support its own weight and hold its shape but also shares some properties of liquids, such as shape conformity to something applying pressure to it, or the ability to flow under pressure. Semi-solids are characterized by a three-dimensional structure that is sufficient to impart solid-like character to the undisturbed system but that is easily broken down and realigned under an applied force. Semi-solids have a rigidity and viscosity intermediate between a solid and a liquid. Preferred semi-solid compositions are foams, gels and lotions, preferably low viscosity gels and lotions. However, liquid compositions are preferred, especially liquid compositions that are solutions or suspensions of anti-PD-L1 antibodies and/or anti-PD-1 antibodies, i.e. more preferably comprising anti-PD-L1 antibodies and/or anti-PD-1 antibodies in a liquid carrier. Preferred liquid carriers are water or aqueous solutions, most preferably aqueous buffers.

If the composition for use in the invention is a liquid composition comprising water, the pH of said composition is preferably in the range of 4.5 to 7.5.

The composition for use in the invention preferably comprises a therapeutically effective amount of anti-PD-L1 antibodies and/or anti-PD-1 antibodies. Such therapeutically effective amount can be administered in one or more instillations into the bladder. For purposes of this invention, a therapeutically effective amount of anti-PD-L1 antibodies and/or anti-PD-1 antibodies is an amount sufficient to accomplish therapeutic treatment together with at least the main treatment, i.e. cystectomy or TUR. Other neoadjuvant or adjuvant treatments may be carried out together with the therapy of the invention, e.g. neoadjuvant radiotherapy, (neo)adjuvant chemotherapy or (neo)adjuvant immunotherapy.

The amount of the composition for use in the invention which is instilled into the bladder may vary according to the bladder volume and size of the bladder of the patient. In general, a volume of about 50 ml of the composition is instilled.

The composition for use in the invention is instilled preferably into the empty bladder through a catheter and is left in the bladder from about 20 minutes to about 3 hours, more preferably from about 30 minutes to about 2 hours, most preferably no less than 1 hour.

In another embodiment, the composition of the invention further comprises hexyl 5-ALA ester (HAL) or a pharmaceutically acceptable salt thereof.

As mentioned above, HAL-guided TUR in patients with NMIBC has led to superior recurrence free survival (RFS) rates and prolonged RFS intervals compared to white light TUR alone. Also, HAL-guided TUR in patients with MIBC seem to have an impact on recurrence free survival: in 268 consecutive patients who underwent cystectomy for bladder cancer it was retrospectively investigated whether patients prior to the cystectomy had undergone HAL-guided TUR or whether TUR was carried out with white light alone. Kaplan-Meier analysis was used to estimate recurrence-free survival (RFS) and overall survival (OS). The 3-year RFS was 69.8% in patients with HAL-guided TUR and 58.2% in patients with white light TUR alone. The 3-year OS was 65.0% in patients with HAL-guided TUR and 56.6%. These results indicate that HAL-guided TUR is associated with improved RFS after cystectomy in patients with MIBC (see G. Gakis et al., Urology Vol. 82, Issue 3, Supplement, Unmoderated Posters, UP.046).

Hence, another embodiment in the therapy according to the invention a composition is used which further comprises hexyl 5-ALA ester (HAL) or a pharmaceutically acceptable salt thereof and wherein after instillation of said composition into the bladder of said patient the inside of said bladder is exposed to light.

Thus in a second aspect the invention provides a method of therapy for bladder cancer in a bladder cancer patient comprising (i) the instillation into the bladder of said patient of a composition comprising a) anti-PD-L1 antibodies and/or anti-PD-1 antibodies and b) hexyl 5-ALA ester (HAL) or a pharmaceutically acceptable salt thereof and (ii) exposing the inside of said bladder to light.

In an alternative second aspect, the invention provides a composition comprising a) anti-PD-L1 antibodies and/or anti-PD-1 antibodies and b) hexyl 5-ALA ester (HAL) or a pharmaceutically acceptable salt thereof for use in a method of therapy for bladder cancer, said therapy comprising (i) instillation of said composition into the bladder of a patient with bladder cancer and (ii) exposing the inside of said bladder to light.

The term "5-ALA" denotes 5-aminolevulinic acid, i.e. 5-amino-4-oxo-pentanoic acid.

The term "hexyl 5-ALA ester" (HAL) denotes n-hexyl aminolevulinate, i.e. n-hexyl 5-amino-4-oxo-pentanoate.

The term "pharmaceutically acceptable salt" denotes a salt that is suitable for use in the dry pharmaceutical product and which fulfils the requirements related to for instance safety, bioavailability and tolerability (see for instance P. H. Stahl et al. (eds.) Handbook of Pharmaceutical Salts, Publisher Helvetica Chimica Acta, Zurich, 2002).

The synthesis of hexyl 5-ALA ester is known in the art and may be prepared as described in e.g. WO 96/28412, the entire contents of which are incorporated herein by reference. Briefly, hexyl 5-ALA ester may be prepared by reaction of 5-ALA with hexanol in the presence of a catalyst, e.g. an acid. Further, hexyl 5-ALA ester hydrochloride is commercially available, e.g. in the form of Hexvix® (Photocure ASA and Ipsen Pharma SA) or Cysview® (Photocure Inc.).

The hexyl 5-ALA ester for use in embodiments of the invention is preferably in the form of a pharmaceutically acceptable salt. Such salts are preferably acid addition salts with pharmaceutically acceptable organic or inorganic acids. Suitable acids include, for example, hydrochloric, nitric, hydrobromic, phosphoric, sulfuric, sulfonic acid and sulfonic acid derivatives, the salts of ALA-esters and the latter acids are described in WO 2005/092838 to Photocure ASA, the entire contents of which are incorporated herein by reference. A preferred acid is hydrochloride acid, HCl.

Synthetic procedures for salt formation are conventional in the art and are for instance described in WO 2005/092838.

The concentration of HAL in the composition for use in the invention is conveniently in the range of 0.1 to 5% by weight of the total weight of the composition or the equivalent concentration of a pharmaceutically acceptable salt of HAL, preferably 0.15 to 3.5%, and most preferably 0.17%. In a most preferred embodiment, the hydrochloride salt of HAL is used in the composition at a concentration of 0.2%.

In a preferred embodiment, the composition comprising a) anti-PD-L1 antibodies and/or anti-PD-1 antibodies and b) HAL or a pharmaceutically acceptable salt thereof for use in the invention is a liquid composition. Preferred liquid carriers are water or aqueous solutions, most preferably aqueous buffers.

In a preferred embodiment, the liquid carrier is an aqueous phosphate buffer, preferably an aqueous phosphate buffer which comprises disodium phosphate dehydrate, potassium dihydrogen phosphate, sodium chloride, hydrochloric acid, sodium hydroxide and water. If the composition comprising a) anti-PD-L1 antibodies and/or anti-PD-1 antibodies and b) HAL or a pharmaceutically acceptable salt thereof for use in the invention is a composition comprising water, said composition has a pH in the range of 4.5 to 7.5, more preferably in the range of 5.7 and 7.2.

The amount of the composition comprising a) anti-PD-L1 antibodies and/or anti-PD-1 antibodies and b) HAL or a pharmaceutically acceptable salt thereof, which is instilled into the bladder, may vary according to the bladder volume and size of the bladder of the patient. In general, a volume of about 50 ml of the composition is instilled.

The composition comprising a) anti-PD-L1 antibodies and/or anti-PD-1 antibodies and b) HAL or a pharmaceutically acceptable salt thereof for use in the invention is instilled preferably into the empty bladder through a catheter and is left in the bladder from about 20 minutes to about 3 hours, more preferably from about 30 minutes to about 2 hours, most preferably no less than 1 hour. If the patient cannot retain the composition for 1 hour, at least 1 hour should be allowed to pass from the instillation of the composition into the bladder to the start of exposing the inside of the bladder to light.

For exposing the inside of the bladder to light, any wavelength of light which is suitable to excite the hexyl 5-ALA ester may be used. Preferred is white light, i.e. visible light with wavelengths of from about 350 to 700 nm and/or blue light, i.e. wavelengths of from about 360 nm to about 450 nm and/or red light, i.e. wavelengths of from about 600 to 670 nm. The term and/or means that e.g. the inside of the bladder is exposed to either white or blue light or to white light and blue light, subsequently and not at the same time. Especially preferred is white light and/or blue light, more preferred white light followed by blue light.

For exposing the inside of the bladder to light, approved cystoscopic light sources are preferred which allow both for white light and blue light irradiation of the inside of the bladder. Such cystoscopes are commercially available, e.g. from Karl Storz (Photodynamic Diagnostic D-Light C (PDD) System), Olympus or Richard Wolf). For red light irradiation, such equipment may be modified with the suitable filters. Such cystoscopic light sources may be rigid or flexible.

The light dose given during irradiation of the inside of the bladder with use of white and blue light may vary but is preferably 0.01 to 100 J/cm2, more preferably 0.03-40 J/cm$^2$ and most preferably 0.1 to 3 J/cm$^2$. For a cystoscopic light source with a output in the range of 47-82 mW such a light dose is provided in about 10 to 30 minutes (calculated based on a 300 cm$^2$ surface area for a human bladder).

The method of therapy according to the invention may be used as a neoadjuvant therapy for bladder cancer patients who are scheduled for a cystectomy.

Hence in one embodiment the invention provides a method of neoadjuvant therapy for bladder cancer in a bladder cancer patient who are scheduled for a cystectomy, said method comprising (i) the instillation into the bladder of said patient of a composition comprising a) anti-PD-L1 antibodies and/or anti-PD-1 antibodies and b) hexyl 5-ALA ester (HAL) or a pharmaceutically acceptable salt thereof and (ii) exposing the inside of said bladder to light.

In an alternative embodiment, the invention provides a composition comprising a) anti-PD-L1 antibodies and/or anti-PD-1 antibodies and b) hexyl 5-ALA ester (HAL) or a pharmaceutically acceptable salt thereof for use in a method of neoadjuvant therapy for bladder cancer, said therapy comprising (i) instillation of said composition into the bladder of a patient with bladder cancer who is scheduled for a cystectomy; and (ii) exposing the inside of said bladder to light.

The time between the method of neoadjuvant therapy of the invention, i.e. instillation into the bladder of a composition comprising anti-PD-L1 antibodies and/or anti-PD-1 antibodies or a) anti-PD-L1 antibodies and/or anti-PD-1 antibodies and b) HAL or a pharmaceutically acceptable salt thereof and exposing the inside of said bladder to light and the cystectomy may vary but is preferably zero to 6 weeks, e.g. zero to 1, 2, 3, 4, 5 or 6 weeks and more preferably zero to 3 weeks, e.g. 1 or 2 weeks. "Zero" means that the cystectomy is carried out directly after the light irradiation is finalized. This has the advantage that the patient is only anaesthetized once.

As mentioned earlier, bladder cancer patients who are scheduled for a cystectomy are those diagnosed with MIBC or NMIBC with a high risk of progression, including multiple recurrent high-grade tumors or high-grade T1 tumors or high-grade tumors with concurrent carcinoma-in-situ (CIS).

The neoadjuvant therapy of the invention may be carried out once or repeatedly prior to the cystectomy, i.e. carried out two or more times, e.g. 3, 4, 5 or 6 times, with a period between the treatments of e.g. 4 days to 4 weeks, e.g. 1, 2 or 3 weeks.

The neoadjuvant therapy of the invention may be carried out prior, simultaneously or after other neoadjuvant therapies, including neoadjuvant radiotherapy, neoadjuvant chemotherapy (intravescial instillation or systemic administration) with e.g. cisplatin, methotrexate, vinblastine, valurubicin, adriamycin, mitomycin C or combinations thereof and neoadjuvant immunotherapy (intravescial instillation or systemic administration) with e.g. BCG.

After cystectomy, the patient may receive systemic adjuvant chemotherapy with e.g. cisplatin, methotrexate, vinblastine, adriamycin, gemcitabine, doxorubicin, epirubicin, cyclophosphamide or combinations thereof Alternatively or in addition thereto, the patient may receive systemic adjuvant immunotherapy with e.g. anti-PD-L1 antibodies and/or anti-PD-1 antibodies.

The method of therapy according to the invention may be used as an adjuvant therapy for bladder cancer patients who undergo TUR, i.e. patients who are diagnosed with NMIBC.

Hence in a further embodiment the invention provides a method of adjuvant therapy for bladder cancer in a bladder cancer patient who undergoes TUR, said method comprising (i) the instillation into the bladder of said patient of a composition comprising a) anti-PD-L1 antibodies and/or anti-PD-1 antibodies and b) hexyl 5-ALA ester (HAL) or a pharmaceutically acceptable salt thereof and (ii) exposing the inside of said bladder to light.

In an further alternative embodiment, the invention provides a composition comprising a) anti-PD-L1 antibodies and/or anti-PD-1 antibodies and b) hexyl 5-ALA ester (HAL) or a pharmaceutically acceptable salt thereof for use in a method of adjuvant therapy for bladder cancer, said therapy comprising (i) instillation of said composition into the bladder of a patient with bladder cancer who undergoes TUR; and (ii) exposing the inside of said bladder to light.

The time between said TUR and the adjuvant therapy of the invention, i.e. instillation into the bladder of a composition comprising anti-PD-L1 antibodies and/or anti-PD-L1 antibodies is preferably zero to 6 weeks, e.g. zero to 1, 2, 3, 4, 5 or 6 weeks and more preferably zero to 3 weeks, e.g. 1 or 2 weeks. "Zero" means that the adjuvant therapy according to the invention is carried out directly after said TUR.

If the adjuvant therapy according to the invention comprises the instillation into the bladder of a composition comprising a) anti-PD-L1 antibodies and/or anti-PD-1 antibodies and b) HAL or a pharmaceutically acceptable salt thereof and exposing the inside of said bladder to light, the TUR may be is carried out simultaneously with said therapy, since the use of HAL enables detection and thus accurate resection of the tumor.

The adjuvant therapy of the invention may be carried out prior, simultaneously or after other neoadjuvant or adjuvant therapies, including (neo)adjuvant radiotherapy, (neo)adjuvant chemotherapy (intravescial instillation or systemic administration) with e.g. cisplatin, methotrexate, vinblastine, valurubicin, adriamycin, mitomycin C or combinations thereof and (neo)adjuvant immunotherapy (intravescial instillation or systemic administration) with e.g. BCG or anti-PD-L1 antibodies and/or anti-PD-1 antibodies.

Various embodiments of the invention are as follows:

Embodiment 1: A method of therapy for bladder cancer in a bladder cancer patient comprising the instillation into the bladder of said patient of a composition comprising anti-PD-L1 antibodies and/or anti-PD-1 antibodies.

Embodiment 2: The method according to embodiment 1, wherein said composition comprises either anti-PD-L1 antibodies or anti-PD-1 antibodies.

Embodiment 3: The method according to embodiment 1, wherein said composition comprises anti-PD-L1 antibodies and anti-PD-1 antibodies.

Embodiment 4: The method according to any of the preceding embodiments, wherein said anti-PD-L1 antibody is MPDL3280A.

Embodiment 5: The method according to any of the preceding embodiments, wherein said anti-PD-1 antibody is pembrolizumab or nivolumab.

Embodiment 6: The method according to any of the preceding embodiments, wherein the composition comprises a therapeutically effective amount of anti-PD-L1 antibodies and/or anti-PD-1 antibodies.

Embodiment 7: The method according to any of the preceding embodiments, wherein the composition is a semi-solid composition or a liquid composition.

Embodiment 8: The method according to any of the preceding embodiments, wherein the composition is a liquid composition, preferably a composition comprising anti-PD-L1 antibodies and/or anti-PD-1 antibodies in a liquid carrier Embodiment 9: The method according to embodiment 8, wherein the liquid carrier is water or aqueous solution, preferably an aqueous buffer.

Embodiment 10: The method according to embodiment 7, wherein the composition is a liquid composition comprising water, the pH of said composition is in the range of 4.5 to 7.5.

Embodiment 11: The method according to any of the preceding embodiments, wherein the composition is instilled into the bladder through a catheter and is left in the bladder from about 20 minutes to about 3 hours.

Embodiment 12: The method according to any of the preceding embodiments wherein the composition further comprises hexyl 5-ALA ester or a pharmaceutically acceptable salt thereof and wherein after instillation of said composition into the bladder of said patient the inside of said bladder is exposed to light.

Embodiment 13: The method according to embodiment 12, wherein the concentration of hexyl 5-ALA ester in the composition is in the range of 0.1 to 5% by weight of the total weight of the composition or the equivalent concentration of a pharmaceutically acceptable salt of HAL.

Embodiment 14: The method according to embodiments 12 and 13, wherein the composition is a liquid composition obtained by reconstitution of lyophilized a) anti-PD-L1 antibodies and/or anti-PD-1 antibodies and b) lyophilized hexyl 5-ALA ester or a pharmaceutically acceptable salt thereof in a liquid carrier, preferably in water or an aqueous solution, most preferably in an aqueous buffer.

Embodiment 15: The method according to any of embodiments 12 to 14, wherein the composition is instilled into the bladder through a catheter and is left in the bladder from about 20 minutes to about 3 hours.

Embodiment 16: The method according to any of the embodiments 12 to 15, wherein the inside of the bladder is exposed to white light and/or blue light and/or red light.

Embodiment 17: The method according to embodiment 16, wherein the inside of the bladder is exposed to white light followed by blue light.

Embodiment 18: The method according to embodiments 1 to 11, wherein said method is a neoadjuvant therapy for bladder cancer patients who are scheduled for a cystectomy.

Embodiment 19: The method according to embodiments 12 to 15, wherein said method is a neoadjuvant therapy for bladder cancer patients who are scheduled for a cystectomy.

Embodiment 20: The method according to embodiments 18 and 19, wherein the time between carrying out said method of neoadjuvant therapy and the cystectomy is zero to 6 weeks.

Embodiment 21: The method according to embodiments 1 to 11, wherein said method is an adjuvant therapy for bladder cancer patients who undergo transurethral resection (TUR).

Embodiment 22: The method according to embodiments 12 to 15, wherein said method is an adjuvant therapy for bladder cancer patients who undergo transurethral resection (TUR).

Embodiment 23: The method according to embodiments 21 and 22, wherein the time between carrying out said method of adjuvant therapy and said TUR is zero to 6 weeks Embodiment 24: The method according to embodiment 22, wherein said method of adjuvant therapy and said TUR are carried out simultaneously.

Embodiment 1a: A composition comprising anti-PD-L1 antibodies and/or anti-PD-1 antibodies for use in a method of therapy for bladder cancer, wherein said composition is instilled into the bladder of a patient with bladder cancer.

Embodiment 2a: The composition for use according to embodiment 1a, wherein said composition comprises either anti-PD-L1 antibodies or anti-PD-1 antibodies.

Embodiment 3a: The composition for use according to embodiment 1a, wherein said composition comprises anti-PD-L1 antibodies and anti-PD-1 antibodies.

Embodiment 4a: The composition for use according to any of the preceding embodiments, wherein said anti-PD-L1 antibody is MPDL3280A.

Embodiment 5a: The composition for use according to any of the preceding embodiments, wherein said anti-PD-1 antibody is pembrolizumab or nivolumab.

Embodiment 6a: The composition for use according to any of the preceding embodiments, wherein the composition comprises a therapeutically effective amount of anti-PD-L1 antibodies and/or anti-PD-1 antibodies.

Embodiment 7a: The composition for use according to any of the preceding embodiments, wherein the composition is a semi-solid composition or a liquid composition.

Embodiment 8a: The composition for use according to any of the preceding embodiments, wherein the composition is a liquid composition, preferably a composition comprising anti-PD-L1 antibodies and/or anti-PD-1 antibodies in a liquid carrier.

Embodiment 9a: The composition for use according to embodiment 8a, wherein the liquid carrier is water or aqueous solution, preferably an aqueous buffer.

Embodiment 10a: The composition for use according to embodiment 7a, wherein the composition is a liquid composition comprising water, the pH of said composition is in the range of 4.5 to 7.5.

Embodiment 11a: The composition for use according to any of the preceding embodiments, wherein the composition is instilled into the bladder through a catheter and is left in the bladder from about 20 minutes to about 3 hours.

Embodiment 12a: The composition for use according to any of the preceding embodiments wherein the composition further comprises hexyl 5-ALA ester or a pharmaceutically acceptable salt thereof and wherein after instillation of said composition into the bladder of said patient, the inside of said bladder is exposed to light.

Embodiment 13a: The composition for use according to embodiment 12a, wherein the concentration of hexyl 5-ALA ester in the composition is in the range of 0.1 to 5% by weight of the total weight of the composition or the equivalent concentration of a pharmaceutically acceptable salt of HAL.

Embodiment 14a: The composition for use according to embodiments 12a and 13a, wherein the composition is a liquid composition obtained by reconstitution of lyophilized a) anti-PD-L1 antibodies and/or anti-PD-1 antibodies and b) lyophilized hexyl 5-ALA ester or a pharmaceutically acceptable salt thereof in a liquid carrier, preferably in water or an aqueous solution, most preferably in an aqueous buffer.

Embodiment 15a: The composition for use according to any of embodiments 12a to 14a, wherein the composition is instilled into the bladder through a catheter and is left in the bladder from about 20 minutes to about 3 hours.

Embodiment 16a: The composition for use according to any of the embodiments 12a to 15a, wherein the inside of the bladder is exposed to white light and/or blue light and/or red light.

Embodiment 17a: The composition for use according to embodiment 16a, wherein the inside of the bladder is exposed to white light followed by blue light.

Embodiment 18a: The composition for use according to embodiments 1a to 11a, wherein said composition is for use in a method of neoadjuvant therapy for bladder cancer patients who are scheduled for a cystectomy.

Embodiment 19a: The composition for use according to embodiments 12a to 15a, wherein said composition is for use in a method of neoadjuvant therapy for bladder cancer patients who are scheduled for a cystectomy.

Embodiment 20a: The composition for use according to embodiments 18a and 19a, wherein the time between carrying out said method of neoadjuvant therapy and the cystectomy is zero to 6 weeks.

Embodiment 21a: The composition for use according to embodiments 1a to 11a, wherein said composition is for use in a method of adjuvant therapy for bladder cancer patients who undergo transurethral resection (TUR).

Embodiment 22a: The composition for use according to embodiments 12a to 15a, wherein said composition is for use in a method of adjuvant therapy for bladder cancer patients who undergo transurethral resection (TUR).

Embodiment 23a: The composition for use according to embodiments 21a and 22a, wherein the time between carrying out said method of adjuvant therapy and said TUR is zero to 6 weeks Embodiment 24a: The composition for use according to embodiment 22a, wherein said method of adjuvant therapy and said TUR are carried out simultaneously.

The invention claimed is:

1. A method of therapy for bladder cancer in a bladder cancer patient comprising the instillation into the bladder of said patient of a composition comprising anti-PD-L1 antibodies and/or anti-PD-1 antibodies, wherein the composition further comprises hexyl 5-ALA ester or a pharmaceutically acceptable salt thereof and wherein after instillation of said composition into the bladder of said patient the inside of said bladder is exposed to light.

2. The method according to claim 1, wherein said composition comprises either anti-PD-L1 antibodies or anti-PD-1 antibodies.

3. The method according to claim 1, wherein said composition comprises anti-PD-L1 antibodies and anti-PD-1 antibodies.

4. The method according to claim 1, wherein said anti-PD-L1 antibody is MPDL3280A.

5. The method according to claim 1, wherein said anti-PD-1 antibody is pembrolizumab or nivolumab.

6. The method according to claim 1, wherein the composition comprises a therapeutically effective amount of anti-PD-L1 antibodies and/or anti-PD-1 antibodies.

7. The method according to claim 1, wherein the composition is a semi-solid composition or a liquid composition.

8. The method according to claim 7, wherein the composition is a liquid composition.

9. The method according to claim 8, wherein the composition comprises anti-PD-L1 antibodies and/or anti-PD-1 antibodies in a liquid carrier.

10. The method according to claim 9, wherein the liquid carrier is water or an aqueous buffer.

11. The method according to claim 7, wherein the composition is a liquid composition comprising water, the pH of said composition is in the range of 4.5 to 7.5.

12. The method according to claim 1, wherein the composition is instilled into the bladder through a catheter and is left in the bladder from about 20 minutes to about 3 hours.

13. The method according to claim 1, wherein the concentration of hexyl 5-ALA ester in the composition is in the range of 0.1 to 5% by weight of the total weight of the composition or the equivalent concentration of a pharmaceutically acceptable salt of HAL.

14. The method according to claim 13, wherein the composition is a liquid composition obtained by reconstitution of lyophilized a) anti-PD-L1 antibodies and/or anti-PD-1 antibodies and b) lyophilized hexyl 5-ALA ester or a pharmaceutically acceptable salt thereof in a liquid carrier.

15. The method according to claim 14, wherein the liquid carrier is water or an aqueous buffer.

16. The method according to claim 13, wherein the composition is instilled into the bladder through a catheter and is left in the bladder from about 20 minutes to about 3 hours.

17. The method according to claim 13, wherein the inside of the bladder is exposed to white light and/or blue light and/or red light.

18. The method according to claim 17, wherein the inside of the bladder is exposed to white light followed by blue light.

19. The method according to claim 1, wherein said method is a neoadjuvant therapy for bladder cancer patients who are scheduled for a cystectomy or an adjuvant therapy for bladder cancer patients who undergo transurethral resection (TUR).

20. The method according to claim 13, wherein said method is a neoadjuvant therapy for bladder cancer patients who are scheduled for a cystectomy or an adjuvant therapy for bladder cancer patients who undergo transurethral resection (TUR).

* * * * *